United States Patent [19]

Henrick et al.

[11] 3,940,444
[45] Feb. 24, 1976

[54] NOVEL KETO-ETHERS

[75] Inventors: Clive A. Henrick; John B. Siddall, both of Palo Alto, Calif.

[73] Assignee: Zoecon Corporation, Palo Alto, Calif.

[22] Filed: May 10, 1974

[21] Appl. No.: 468,856

Related U.S. Application Data

[63] Continuation-in-part of Ser. No. 222,800, Feb. 2, 1972, abandoned, which is a continuation-in-part of Ser. No. 187,897, Oct. 8, 1971, Pat. No. 3,755,411, which is a continuation-in-part of Ser. Nos. 111,650, Feb. 1, 1971, Pat. No. 3,729,486, and Ser. No. 111,770, Feb. 1, 1971, abandoned.

[52] U.S. Cl. .............................................. 260/594
[51] Int. Cl.² .................... C07C 49/20; C07C 49/24
[58] Field of Search .......... 260/593 R, DIG. 44, 594

[56] References Cited
UNITED STATES PATENTS

| | | | |
|---|---|---|---|
| 3,238,260 | 3/1966 | Pasedach et al. | 260/594 |
| 3,252,998 | 5/1966 | Ohloff et al. | 260/594 |
| 3,330,867 | 7/1967 | Saucy | 260/594 |
| 3,439,042 | 4/1969 | Eschenasi | 260/594 |
| 3,453,317 | 7/1969 | Marbett et al. | 260/594 |

OTHER PUBLICATIONS

Slama et al., *Proceeding of the National Academy of Science*, Vol. 54, pp. 411–414, (1965).

Sarmiento et al., *Science*, Vol. 179, pp. 1342–43.

*Primary Examiner*—James O. Thomas, Jr.
*Assistant Examiner*—James H. Reamer
*Attorney, Agent, or Firm*—Donald W. Erickson

[57] ABSTRACT

Aliphatic hydrocarbon substituted aliphatic diolefinic ketones, and derivatives thereof, intermediates therefor, syntheses thereof, and the control of insects.

13 Claims, No Drawings

NOVEL KETO-ETHERS

This is a continuation-in-part of application Ser. No. 222,800, filed Feb. 2, 1972, now abandoned, which is, in turn, a continuation-in-part of application Ser. No. 187,897, filed Oct. 8, 1971, now U.S. Pat. No. 3,755,411, which is a continuation-in-part of applications Ser. No. 111,650, filed Feb. 1, 1971, now U.S. Pat. No. 3,729,486 and Ser. No. 111,770, filed Feb. 1, 1971, now abandoned, the entire disclosures of which are incorporated by reference.

This invention relates to novel aliphatic di-olefinic compounds, intermediates therefore, syntheses thereof, and the control of insects. More particularly, the novel di-olefinic compounds of the present invention are represented by the following formula:

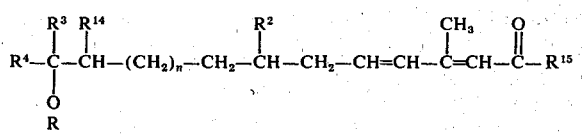

wherein,
R is hydrogen, methyl or ethyl;
n is zero or the positive integer one;
each of $R^2$, $R^3$ and $R^4$ is methyl or ethyl;
$R^{14}$ is hydrogen or methyl; and
$R^{15}$ is lower alkyl of one to three carbon atoms.

The compounds of formula A are useful for the control of insects. The utility of these compounds as insect control agents is believed to be attributable to their juvenile hormone activity. They are preferably applied to the immature insect, namely — during the embryo, larvae or pupae stage in view of their effect on metamorphosis and otherwise cause abnormal development leading to death or inability to reproduce. These compounds are effective control agents for Hemipteran, such as Lygaedae, Miridae and Pyrrhocoridae; Lepidopteran, such as Pyralidae, Noctuidae and Gelechiidae; Coleopteran, such as Tenebrionidae, Crysomelidae and Dermestidae; Dipteran, such as mosquitos, flies; Homopteran, such as aphids; and other insects. The compounds can be applied at low dosage levels of the order of 0.001 μg. to 25.0 μg. per insect. Suitable carrier substances include liquid or solid carriers, such as water, acetone, xylene, mineral or vegetable oils, talc, vermiculite, natural and synthetic resins and silica. Treatment of insects in accordance with the present invention is accomplished by spraying, dusting or exposing the insects to the vapor of the compounds of formula A. Generally, a concentration of less than 25% of the active compound is employed. The formulations can include insect attractants, emulsifying agents or wetting agents to assist in the application and effectiveness of the active ingredient. In the application of the compounds, there is generally employed a mixture of the α,β-trans and cis isomers. Mixtures containing predominately the α,β-trans isomer are preferred.

In the description hereinafter, each of R, $R^2$—$R^4$, $R^{14}$—$R^{15}$, and n is as defined hereinabove, unless otherwise specified.

Compounds of the following formula B serve as precursors for the preparation of the compounds of formula A.

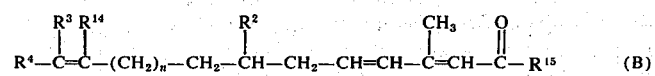

The ketones of formula A and B can be prepared by treating an acid or ester of formula C or D ($R^7$ is hydrogen or lower alkyl) with the appropriate organo-lithium reagent, the organo group corresponding to the ketone moiety desired. The reaction is generally carried out in an organic solvent such as an ether solvent. In addition, acid halides of the acids of formula C and D, particularly the acid chloride, can be used for the preparation of ketones by reaction with lithium diorganocopper, e.g. lithium dimethylcopper, using the procedure of Posner and Whitten, Tetrahedron Letters, No. 53, 4647 (1970).

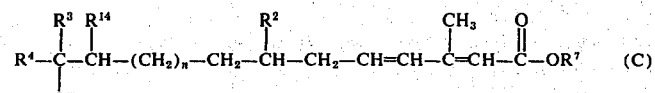

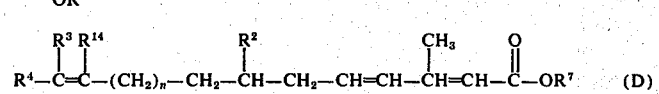

Syntheses of acids and esters of formulas C and D are fully described in, for example, U.S. Pat. Nos. 3,755,411 and 3,732,282, the entire disclosures of which are incorporated by reference.

The compounds of formula A in which R is hydrogen can be prepared by the addition of water to the terminal olefinic bond of a compound of formula B using a mercuric salt followed by reduction of the oxy-mercurial intermediate in situ. Suitable mercuric salts include mercuric acetate, mercuric nitrite, mercuric trifluoroacetate, mercuric acylates and mercuric halides. Suitable reducing agents include the borohydrides, hydrazine and sodium amalgam. See Brown and Rei, J. Am. Chem. Soc. 91, 5654 (1969); Brown et al., J. Am. Chem. 12, 191 (January, 1969). By conducting the reaction in the presence of an alcohol (R-OH) such as methanol, ethanol, or isopropyl alcohol, and the like, the corresponding ether is prepared.

The term "lower alkyl" refers to an alkyl group having a chain length of one to three carbon atoms.

In addition to the compounds of the present invention having activity useful for the control of insects, the compounds of formula A are useful in perfumery compositions in view of their odor-imparting properties.

The presence of an olefinic bond at the $\alpha,\beta$ and $\delta,\sigma$ positions relative to the carbonyl portion of the compound, of formula A gives rise to four isomers, each of which is embraced by the present invention. As mentioned above, a mixture of isomers is suitably employed for the control of insects such as a mixture containing the trans-$\alpha,\beta$,trans-$\delta,\sigma$ isomer and the cis-$\alpha,\beta$,trans-$\delta,\sigma$ isomer. The selection of appropriate conditions and reactants to favor formation of one isomer over another will be apparent to those of ordinary skill in the art. In the specific examples hereinafter, when isomerism is not specified, it is understood to include a mixture of isomers which, if desired, can be separated using known separation methods. Hereafter, when only one designation of configuration is given, the designation refers to position $\alpha,\beta$ and the configuration is taken to be trans at position $\delta,\sigma$ when not otherwise specified. The use of "trans/cis" and "cis/trans" is with reference to position $\alpha,\beta$ and indicates a mixture of isomers. Examples of compounds included within formulas C and D useful for preparation of compounds of the present invention are the following.

ethyl 3,7,11-trimethyldodeca-2,4,10-trienoate
methyl 3,7,11-trimethyldodeca-2,4,10-trienoate
ethyl 3,7,11-trimethyltrideca-2,4,10-trienoate
ethyl 3,11-dimethyl-7-ethyltrideca-2,4,10-trienoate
ethyl 7,11-diethyl-3-methyltrideca-2,4,10-trienoate
ethyl 3,7,10-trimethylundeca-2,4,9-trienoate
ethyl 3,7,10-trimethyldodeca-2,4,9-trienoate
ethyl 3,6,10-trimethylundeca-2,4,9-trienoate
methyl 11-hydroxy-3,7,11-trimethyldodeca-2,4-dienoate
methyl 11-hydroxy-3,7,11-trimethyltrideca-2,4-dienoate
methyl 11-hydroxy-3,11-dimethyl-7-ethyltrideca-2,4-dienoate
methyl 11-hydroxy-3-methyl-7,11-diethyltrideca-2,4-dienoate
methyl 10-hydroxy-3,7,10-trimethylundeca-2,4-dienoate
methyl 10-hydroxy-3,7,10-trimethyldodeca-2,4-dienoate
methyl 11-ethoxy-3,7,11-trimethyldodeca-2,4-dienoate
methyl 11-ethoxy-3,7,11-trimethyltrideca-2,4-dienoate
methyl 11-ethoxy-3,11-dimethyl-7-ethyltrideca-2,4-dienoate
methyl 11-ethoxy-3-methyl-7,11-diethyltrideca-2,4-dienoate
methyl 10-ethoxy-3,7,10-trimethylundeca-2,4-dienoate
methyl 10-ethoxy-3,7,10-trimethyldodeca-2,4-dienoate
methyl 3,7,10,11-tetramethyldodeca-2,4,10-trienoate
methyl 3,7,9,10-tetramethylundeca-2,4,9-trienoate
methyl 11-methoxy-3,7,11-trimethyldodeca-2,4-dienoate
methyl 11-methoxy-3,7,10,11-tetramethyldodeca-2,4-dienoate
methyl 11-methoxy-3,7,10,11-tetramethyltrideca-2,4-dienoate
methyl 10-methoxy-3,7,9,10-tetramethylundeca-2,4-dienoate The following examples are provided to illustrate the practice of the present invention. Temperature is given in degrees Centigrade.

EXAMPLE 1

To a stirred solution of 2.4 g. of 3,7,11-trimethyldodeca-2,4,10-trienoic acid in 20 ml. of dry ether is added slowly, at 0°, 23 ml. of a one molar solution of ethyl lithium in benzene. After about 3 hours at 20°, the mixture is poured into iced 1N hydrochloric acid (100 ml.) with vigorous stirring. The ether layer is separated, combined with ethereal washings of the aqueous phase, washed with water, saturated potassium bicarbonate and then saturated brine, dried over magnesium sulfate and concentrated under reduced pressure to yield 5,9,13-trimethyltetradeca-4,6,12-trien-3-one, which can be purified by chromatography.

By using methyl lithium in the above process in place of ethyl lithium, there is prepared 4,8,12-trimethyltrideca-3,5,11-trien-2-one.

The process of this Example is repeated using each of the acids under Column I as the starting material to prepare the respective ketone of Column II.

I 3,7,11-trimethyltrideca-2,4,10-trienoic acid
3,11-dimethyl-7-ethyltrideca-2,4,10-trienoic acid
7,11-diethyl-3-methyltrideca-2,4,10-trienoic acid
3,7,10-trimethylundeca-2,4,9-trienoic acid'
3,7,10-trimethyldodeca-2,4,9-trienoic acid
3,7,10,11-tetramethyldodeca-2,4,10-trienoic acid
11-methoxy-3,7,11-trimethyldodeca-2,4-dienoic acid
10-methoxy-3,7,10-trimethylundeca-2,4-dienoic acid
11-ethoxy-3,7,11-trimethyldodeca-2,4-dienoic acid

II 5,9,13-trimethylpentadeca-4,6,12-trien-3-one
5,13-dimethyl-9-ethylpentadeca-4,6,12-trien-3-one
9,13-diethyl-5-methylpentadeca-4,6,12-trien-3-one
5,9,12-trimethyltrideca-4,6,11-trien-3-one
5,9,12-trimethyltetradeca-4,6,11-trien-3-one
5,9,12,13-tetramethyltetradeca-4,6,12-trien-3-one
13-methoxy-5,9,13-trimethyltetradeca-4,6-dien-3-one
12-methoxy-5,9,12-trimethyltrideca-4,6-dien-3-one
13-ethoxy-5,9,13-trimethyltetradeca-4,6-dien-3-one Following the above procedure, each of the acids under Column I is reacted with methyl lithium to prepare the respective methyl ketones:

4,8,12-trimethyltetradeca-3,5,11-trien-2-one
4,12-dimethyl-8-ethyltetradeca-3,5,11-trien-2-one
8,12-diethyl-4-methyltetradeca-3,5,11-trien-2-one
4,8,11-trimethyldodeca-3,5,10-trien-2-one
4,8,11-trimethyltrideca-3,5,10-trien-2-one, etc.

Following the process of this example, each of 11-methoxy-3,7,10,11-tetramethyldodeca-2,4-dienoic acid and 3,7,9,10-tetramethylundeca-2,4,10-trienoic acid is reacted with ethyl lithium to prepare 13-methoxy-5,9,12,13-tetramethyltetradeca-3,6-dien-3-one and 5,9,11,12-tetramethyltrideca-4,6,12-trien-3-one, respectively.

EXAMPLE 2

To a mixture of 1.9 g. of mercuric acetate, 6 ml. of water and 20 ml. of tetrahydrofuran is added 1.49 g. of 5,9,13-trimethyltetradeca-4,6,12-trien-3-one slowly.

After addition is complete, the reaction mixture is stirred for about 20 minutes. The mixture is cooled to about 0° and 6 ml. of aqueous sodium hydroxide (3 molar) is added followed by 0.49 g. of sodium borohydride in aqueous sodium hydroxide (about 3 molar). The mixture is stirred for about 30 minutes. The mixture is then decanted, concentrated, diluted with water and then extracted with ether. The ethereal extract is washed with water, dried over magnesium sulfate and the product chromatographed on silica to yield 13-hydroxy-5,9,13-trimethyltetradeca-4,6-dien-3-one.

The above process is repeated using each of the compounds under Column III as the starting material to prepare the respective hydroxyl substituted compounds under Column IV.

III 5,9,13-trimethylpentadeca-4,6,12-trien-3-one
5,13-dimethyl-9-ethylpentadeca-4,6,12-trien-3-one
4,8,12-trimethyltetradeca-3,5,11-trien-2-one
4,8,12-trimethyltrideca-3,5,11-trien-2-one
4,12-dimethyl-8-ethyltetradeca-3,5,11-trien-2-one

IV 13-hydroxy-5,9,13-trimethylpentadeca-4,6-dien-3-one
13-hydroxy-5,13-dimethyl-9-ethylpentadeca-4,6-dien-3-one
12-hydroxy-4,8,12-trimethyltetradeca-3,5-dien-2-one
12-hydroxy-4,8,12-trimethyltrideca-3,5-dien-2-one
12-hydroxy-4,12-dimethyl-8-ethyltetradeca-3,5-dien-2-one Other hydroxy-substituted di-unsaturated ketones of formula A can be prepared by the process of this example using tri-unsaturated ketones of formula B or the acetal or ketal thereof as the precursor.

EXAMPLE 3

To a solution of 2 g. of 5,9,13-trimethyltetradeca-4,6,12-trien-3-one in 20 ml. of ethanol, cooled to 0° by an ice-bath, is added a suspension of 2.32 g. of mercuric acetate in 50 ml. of ethanol over 15 minutes. The reaction mixture is stirred for 2 hours and then with cooling, to −20°, 1.22 g. of potassium hydroxide in 20 ml. of ethanol is added. Then 0.139 g. of sodium borohydride is added in small portions and stirring continued for 30 minutes at −20°. The solution is decanted, then concentrated to half volume, diluted with 100 ml. of water and extracted with ether (3 × 50). The ethereal phase is washed with water, dried over magnesium sulfate and the crude product chromatographed on silica to yield 13-ethoxy-5,9,13-trimethyltetradeca-4,6-dien-3-one.

The process of this example is repeated using each of the compounds under Column III as the starting material to prepare the respective 11-ethoxy-substituted compound under Column V.

V 13-ethoxy-5,9,13-trimethylpentadeca-4,6-dien-3-one
13-ethoxy-5,13-dimethyl-9-ethylpentadeca-4,6-dien-3-one
12-ethoxy-4,8,12-trimethyltetradeca-3,5-dien-2-one
12-ethoxy-4,8,12-trimethyltrideca-3,5-dien-2-one
12-ethoxy-4,12-dimethyl-8-ethyltetradeca-3,5-dien-2-one Other ethoxy-substituted di-unsaturated ketones of formula A can be prepared by the process of this example using tri-unsaturated ketones of formula B or the acetal or ketal thereof as the precursor.

By repeating the procedure of this example using methanol in place of ethanol, the respective ethers are obtained, that is 13-methoxy-5,9,13-trimethyltetra-4,6-dien-3-one, etc.

EXAMPLE 4

Following the procedure of Example 1, n-propyl lithium is reacted with each of
11-methoxy-3,7,11-trimethyldodeca-2,4-dienoic acid, and
3,7,11-trimethyldodeca-2,4,10-trienoic acid to yield
14-methoxy-6,10,14-trimethylpentadeca-5,7-dien-4-one and
6,10,14-trimethylpentadeca-5,7,13-trien-4-one.

EXAMPLE 5

To a solution of 2.00 g. of 11-methoxy-3,7,11-trimethyldodeca-2,4-dienoic acid in 75 ml. ether at −5° under nitrogen is added 15.7 ml. of a 0.95 molar solution of ethyllithium in benzene. The reaction mixture is stirred for 5 hours at −5° to 0°C and overnight at room temperature.

The reaction mixture is poured into saturated aqueous ammonium chloride solution, organic layer is separated, is washed twice with saturated aqueous sodium chloride, is dried over calcium sulfate and the solvent is removed to yield 1.63 g. of crude product, which is purified by preparative thin-layer chromatography (30% ether/70% hexane) to yield 13-methoxy-5,9,13-trimethyltetradeca-4,6-dien-3-one.

EXAMPLE 6

To a solution of 3.35 g. of 11-hydroxy-3,7,11-trimethyldodeca-2,4-dienoic acid in 50 ml. ether at −20°C under nitrogen is added dropwise 59.1 ml. of a 0.67 molar solution of ethyllithium in benzene. The reaction mixture is allowed to warm to room temperature and is stirred overnight. The reaction mixture is then taken up in a mixture of ether and saturated aqueous ammonium chloride. The organic layer is separated, is washed with saturated aqueous ammonium chloride, 5% aqueous sodium bicarbonate, water, and saturated sodium chloride, is dried over calcium sulfate, and the solvent is removed to yield 13-hydroxy-5,9,13-trimethyltetradeca-4,6-dien-3-one which is purified by preparative thin layer chromatography (50% ether/hexane).

Three groups of 30 each of Aedes aegypti, fourth instar larvae, in 50 ml. of tap water containing a few drops of liver powder suspension, room temperature of 28° and photoperiod of 18 hours, are treated with 12-ethoxy-4,8,12-trimethyltrideca-3,5-dien-2-one (about 60% trans,trans) using 50 microliters of acetone as the carrier at three different dosage levels. A fourth group is maintained under identical conditions. Each group is scored after 7 days by the following system: 0 = normal adult, completly emerged (free or floating); 1 = abnormal adult, nonviable; 2 = incompletely emerged adult; 3 = dead pupa; and 4 = dead larvae. For each group the total number of animals in classes 1–4 is divided by 30 to determine the percentage result. The $ID_{50}$ is computed by plotting on semi-logarithmic paper, the dose on the horizontal axis and the percentage response on the vertical axis. The $ID_{50}$ was determined to be less than 1.0 ppm. Each of the larvae of the control group developed into normal adults.

Although not intending to be limited by a theoretical explanation, the effectiveness of the compounds of the present invention to control insects is attributed to the property of these novel compounds to mimic the activity of juvenile hormone. While the methods of applying and carriers for conventional insecticides are usually adaptable to the practical use of the compounds of the present invention, the mechanism of action of these novel compounds is unlike that of conventional insecticides. Whereas conventional insecticides are dependent upon direct knockdown effect, toxity effect or paralyzing effect, the compounds of this invention achieve control by reason of their ability to inhibit metamorphosis, inhibit reproduction due to abnormal development, break diapause at an unfavorable time, or act as a direct insecticide, particularly at the embryo stage and larvae stage. Treatment of insects in accordance with the present invention can be achieved via ingestion of the active compound in the normal food of the insect and by topical application, that is — by contact of the epidermis of the insect as by spraying the insect and habitat of the insect or exposure to vapors of the active compound which penetrate into the insect.

The compounds of the present invention can be used in conjuction with other juvenile hormone active substances and conventional insecticides to obtain a broad spectrum of activity or to provide more immediate effect on very heterogeneous populations. Typical insecticides which may be combined with the compounds of the present invention are Malathion, Sevin, Vapona, Abate, synthetic and natural pyrethrins, and the like and usually within the ratio of between 10:1 to 1:10, by weight.

What is claimed is:

1. A compound selected from those of the following formula:

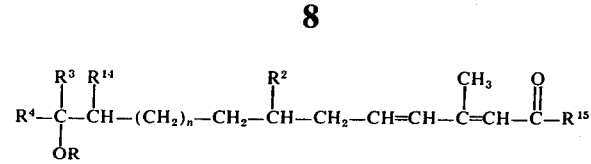

wherein,

R is hydrogen, methyl or ethyl;

$n$ is zero or one;

each of $R^2$, $R^3$ and $R^4$ is methyl or ethyl;

$R^{14}$ is hydrogen or methyl; and $R^{15}$ is lower alkyl of one to three carbon atoms.

2. A compound according to claim 1 wherein R is hydrogen or methyl.

3. A compound according to claim 2 wherein each of $R^2$, $R^3$ and $R^4$ is methyl and $R^{14}$ is hydrogen.

4. A compound according to claim 3 wherein n is one.

5. The compound 13-methoxy-5,9,13-trimethyltetradeca-4,6-dien-3-one according to claim 4.

6. The compound 12-methoxy-5,9,12-trimethyltrideca-4,6-dien-3-one according to claim 3.

7. The compound 13-ethoxy-5,9,13-trimethyltetradeca-4,6-dien-3-one, according to claim 1.

8. The compound, 13-methoxy-2,5,9,13-tetramethyltetradeca-4,6-dien-3-one, according to claim 4.

9. The compound 13-ethoxy-5,9,13-trimethylpentadeca-4,6-dien-3-one according to claim 1.

10. The compound 12-ethoxy-4,8,12-trimethyltrideca-3,5-dien-2-one according to claim 1.

11. The compound 14-methoxy-6,10,14-trimethylpentadeca-5,7-dien-4-one according to claim 4.

12. The compound 13-ethoxy-5,13-dimethyl-9-ethylpentadeca-4,6-dien-3-one according to claim 1.

13. The compound 13-hydroxy-5,9,13-trimethyltetradeca-4,6-dien-3-one according to claim 4.

* * * * *